(12) United States Patent
Ramachandran et al.

(10) Patent No.: US 9,165,094 B2
(45) Date of Patent: Oct. 20, 2015

(54) SYSTEMS AND METHODS FOR DYNAMICALLY MODELING THE HUMAN INTERNAL PELVIC ENVIRONMENT FOR PRODUCT INTERACTIONS

(71) Applicant: The Procter & Gamble Company, Cincinnati, OH (US)

(72) Inventors: Alexzandra Joan Ramachandran, Cincinnati, OH (US); Ryo Nmn Minoguchi, Cincinnati, OH (US); Diana Lynne Gann, Lebanon, OH (US); Dean Larry Duval, Lebanon, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 211 days.

(21) Appl. No.: 13/929,117

(22) Filed: Jun. 27, 2013

(65) Prior Publication Data
US 2015/0006121 A1     Jan. 1, 2015

(51) Int. Cl.
*G06F 9/455*     (2006.01)
*G06F 17/50*     (2006.01)

(52) U.S. Cl.
CPC .................. *G06F 17/5009* (2013.01)

(58) Field of Classification Search
CPC ............ G06F 17/5018; G06F 17/5036; G06F 17/5009; G06F 2217/16; G05B 17/02
USPC .............................................. 703/2
See application file for complete search history.

(56) References Cited

U.S. PATENT DOCUMENTS

| | | | |
|---|---|---|---|
| 7,174,774 B2 * | 2/2007 | Pawar et al. | 73/73 |
| 7,715,938 B2 * | 5/2010 | Gilbert et al. | 700/119 |
| 7,937,249 B2 | 5/2011 | Osborn et al. | |
| 8,392,159 B2 | 3/2013 | Osborn et al. | |
| 2007/0016391 A1 | 1/2007 | Minoguchi et al. | |

FOREIGN PATENT DOCUMENTS

| | | |
|---|---|---|
| KR | 100628252 B1 | 9/2006 |
| WO | WO2004081899 A1 | 9/2004 |

OTHER PUBLICATIONS

Alexandre, F., 3D reconstruction of pelvic floor for numerical simulation purpose, Proceedings of VIPIMAGE 2007—1st ECCOMAS Thematic Conference on Computational Vision and Medical Image Processing, pp. 359-362 (2008) Abstract.

(Continued)

*Primary Examiner* — Saif Alhija
(74) *Attorney, Agent, or Firm* — Andrew J. Hagerty

(57) ABSTRACT

Included are embodiments for dynamically modeling a human internal pelvic environment for product interactions. Some embodiments include creating a computational simulation of biomechanical interactions between feminine product and a pelvic region for a predetermined body type and simulating dynamic contraction of pelvic floor muscles and movement of surrounding parts of the pelvic region as would be experienced in normal use of the feminine product. Similarly, some embodiments are configured to determine, from the simulation, positional changes and effectiveness of the feminine product, determine whether the feminine product is acceptable, and in response to determining that the feminine product is not acceptable, alter a feature of the feminine product. In some embodiments, in response to determining that the feminine product is acceptable, data related to the feminine product being acceptable may be output.

8 Claims, 8 Drawing Sheets

(56) References Cited

OTHER PUBLICATIONS

Bastiaanssen, E.H.C., et al., A Myocybernetic Model of the Lower Urinary Tract, J of Theorectical Biology, vol. 178, pp. 113-133 (1996).

Bastiaanssen, E.H.C., et al., State-space Analysis of a Myocybernetic Model of the Lower Urinary Tract, J of Theorectical Biology, vol. 180(3), pp. 215-227 (1996).

Bellemare, et al., Toward the Simulation of the Strain of Female Pelvic Organs, Proceedings of the 29th Annual International Conference of the IEEE EMBS Cité Internationale, Lyon, France, pp. 2752-2755 (Aug. 23-26, 2007).

El-Asfoury, M.S., et al., Static and Dynamic Three-Dimensional Finite Element Analysis of Pelvic Bone, World Academy of Science, Engineering and Technology, vol. 57, pp. 789-795 (2009).

Engel, A.F., et al., The acute effect of straining on pelvic floor neurological function, Intl J of Colorectal Disease, vol. 9, pp. 8-12 (1994).

Jin, Q., et al., Dynamics analysis of bladder-urethra system based on CFD, Frontiers of Mechanical Engineering in China, vol. 5(3), pp. 336-340 (2010).

Martins, J.A.C., et al., Finite element studies of the deformation of the pelvic floor, Annals of the New York Academy of Sciences, vol. 1101, pp. 316-334 (2007).

Neptune, R.R., et al., Forward Dynamics Simulations Provide Insight Into Muscle Mechanical Work During Human Locomotion, Exerc. Sport Sci. Rev., vol. 37(4), pp. 203-210 (2009).

Noakes, K.F., et al., Subject specific finite elasticity simulations of the pelvic floor, J. of Biomechanics, vol. 1, pp. 3060-3065 (2008).

Okamoto, N., et al., Enterocele associated with rectocele revealed by dynamic pelvic CT, Abdominal Imaging, vol. 30, pp. 679-681 (2005).

Pirro, N., et al., Preliminary results and perspectives for female patient-specific modeling of the pelvic organs, Pelv Perineol, vol. 4, pp. 15-21 (2009).

Shao, Q., et al., An Emg-Driven Forward Simulation of Single Support Phase During Gait, Comput Biol Med.; vol. 39(12); pp. 1083-1088 (2009).

Zhang, X.J., et al., Computational Fluid Dynamics Model of Bladder-Urethra System for SUI, WCB, IFMBE Proceedings, vol. 31, pp. 1495-1498 (2010).

\* cited by examiner

SYSTEMS AND METHODS FOR DYNAMICALLY MODELING THE HUMAN INTERNAL PELVIC ENVIRONMENT FOR PRODUCT INTERACTIONS

FIELD OF THE INVENTION

The present application relates generally to systems and methods for dynamically modeling the human internal pelvic environment and, specifically, to embodiments for designing a feminine product that accounts for the wearers body type and physical activity.

BACKGROUND OF THE INVENTION

Historically, many feminine products have taken a one-size-fits-all approach. Many feminine product designers have created feminine products that fit the "average woman." While such a solution may accommodate many women and reduce production costs associated with a single design, oftentimes women differ in shapes and sizes and thus the feminine products designed in this manner fail to provide the desired wearer experience. Specifically, some women may experience discomfort while placing, wearing, or removing these products, while others may not receive the desired protection.

Additionally, many women differ in types and levels of activities. While a particular feminine product may provide the desired results during sleep or work, these products may provide less than desired comfort or protection during different activities. Similarly, some women may have different life experiences, such as activities that cause large or variable deformation in the pelvic cavity, child birth, etc. that affect the type and shape of feminine products that provide the desired comfort and results. Accordingly, there is a need for dynamically modeling the human internal pelvic environment to account for such activities and body types.

SUMMARY OF THE INVENTION

Included are embodiments for dynamically modeling a human internal pelvic environment for product interactions. Some embodiments include creating a computational simulation of biomechanical interactions between feminine product and a pelvic region for a predetermined body type and simulating dynamic contraction of pelvic floor muscles and movement of surrounding parts of the pelvic region as would be experienced in normal use of the feminine product. Acceptability may be assessed relative to existing products and may include comfort and performance relating to initial placement, placement stability, insertion, soiling incidence, urine leakage, menses leakage, tissue displacement, stress distribution, compression of tissues and adhesion. Similarly, some embodiments are configured to determine, from the simulation, positional changes and effectiveness of the feminine product, determine whether the feminine product is acceptable, and in response to determining that the feminine product is not acceptable, alter a feature of the feminine product. In some embodiments, in response to determining that the feminine product is acceptable, data related to the feminine product being acceptable may be output.

Also included are embodiments of a method. Some embodiments of the method are configured to receive user input regarding a desired product type of a feminine product, a desired model body type, and a desired activity, simulate dynamic contraction of pelvic floor muscles and movement of surrounding parts as would be experienced in normal use of the feminine product, and determine whether the feminine product that meets the desired product type, the desired body type, and the desired activity is available for purchase. In response to determining that the feminine product that meets the desired product type, the desired body type, and the desired activity is available for purchase some embodiment are configured to output an identification of the feminine product to a user. In some embodiments, in response to determining that the feminine product is not available for purchase, data related to the user input to a different computing device may be sent for designing the feminine product and an output may be sent to the user indicating that no product is currently available.

Also included are embodiments of a non-transitory computer-readable medium. Some embodiments of the non-transitory computer-readable medium include logic that causes a computing device to create a computational simulation of biomechanical interactions between feminine product and a pelvic region for a predetermined body type, determine an activity that a wearer of the feminine product would engage, and simulate dynamic movement of an area of the pelvic region as would be experienced in the activity. In some embodiments the logic causes the computing device to determine, from the simulation, positional changes and effectiveness of the feminine product, determine whether the feminine product is acceptable, and in response to determining that the feminine product is not acceptable, alter a feature of the feminine product. In some embodiments, in response to determining that the feminine product is acceptable, the logic causes the computing device to output data related to the feminine product being acceptable.

BRIEF DESCRIPTION OF THE DRAWINGS

It is to be understood that both the foregoing general description and the following detailed description describe various embodiments and are intended to provide an overview or framework for understanding the nature and character of the claimed subject matter. The accompanying drawings are included to provide a further understanding of the various embodiments, and are incorporated into and constitute a part of this specification. The drawings illustrate various embodiments described herein, and together with the description serve to explain the principles and operations of the claimed subject matter.

DETAILED DESCRIPTION OF THE INVENTION

Embodiments disclosed herein include systems and methods for dynamically modeling the human internal pelvic environment for product interactions. Specifically, there are a variety of feminine products available on the market today, including tampons, pessaries, rings, feminine condoms, pelvic muscle trainers, pelvic muscle stimulators, vaginal pressure sensors, pelvic muscle electromyogram sensors, vaginal dilators, ultrasound probes, balloon catheters, etc. Such feminine product may be placed in the vagina to provide one or more intended benefits for a wearer. To fully provide the intended benefits for the wearer, the feminine product should be designed for delivery to an intended region of the vagina, maintain its position, and function in the intended manner.

The vagina has a collapsed tube-like structure composed of highly deformable soft tissues. It is located in the pelvic floor region and is surrounded by the other organs in the pelvic floor region such as the uterus, the cervix, the bladder, the urethra, and the rectum. The pelvic floor is primarily composed of muscular tissues supporting the pelvic organs with a hammock-like structure, which allows the organs in the pelvic floor to be displaced easily with internal and/or external stressing. This stressing is often a result activities or diaphragm movements that change the conditions in that region. Because of such existing vaginal characteristics and the pelvic floor including the vagina, once the feminine product is introduced into the vagina, the feminine product generates complex mechanical interactions with the vagina and the surrounding organs, and creates a certain environment under which the feminine product should be designed to deliver its functionality or provide information about the environment.

A computational simulation of biomechanical interactions between the feminine product and the pelvic floor including the vagina is disclosed herein and may be useful to understand such complex mechanical interactions among the feminine product, the vagina, and the surrounding organs in the pelvic floor, and enable efficient development of the device by reducing iterations of physical prototyping of the device and testing of the device using human subjects. As such, embodiments described herein may be utilized to simulate the mechanical interactions to determine effectiveness of such product designs, as well as determine better designs, based on a desired body type, desired body condition, desired activity, etc.

Figure 1:
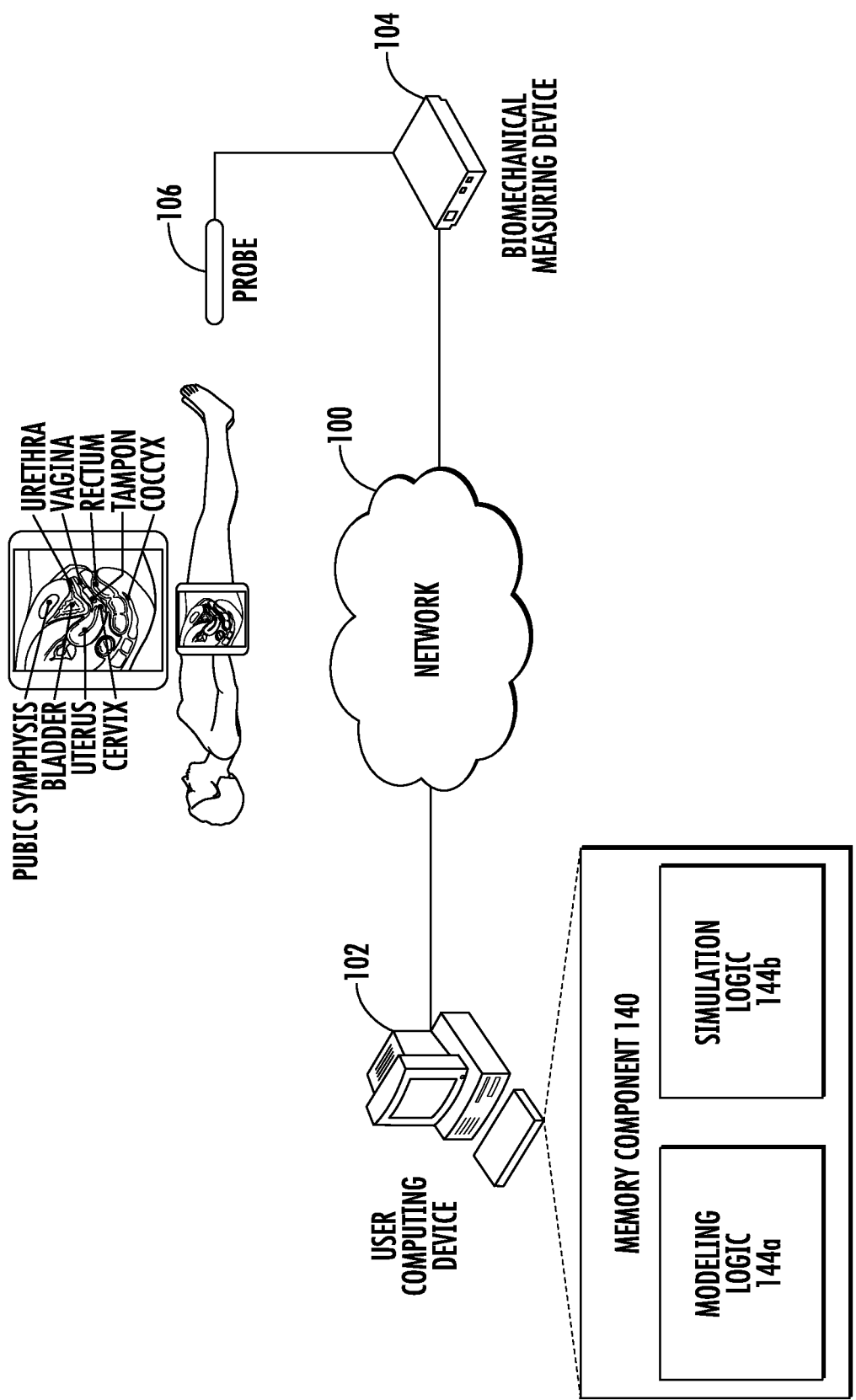
FIG. 1 depicts a computing environment for dynamically modeling the human internal pelvic region, according to embodiments disclosed herein.

Referring now to the drawings, FIG. 1 depicts a computing environment for dynamically modeling the human internal pelvic region, according to embodiments disclosed herein. As illustrated, a network 100 may be coupled to a user computing device 102 and a biomechanical measuring device 104 and a probe 106. The network 100 may include any wide area and/or local area network, such as the internet, a mobile communications network, a satellite network, a public service telephone network (PSTN) and/or other network for facilitating communication between devices. If the network 100 includes a local area network, the local area network may be configured as a corporate network and/or other open or closed network that is coupled to a wide area network.

Accordingly, the user computing device 102 may include a personal computer, laptop computer, tablet, mobile communications device, database, and/or other computing device that is accessible by a feminine product designer. Specifically, the feminine product designer may create a virtual representation of a feminine product and simulate the dynamic environment that the feminine product will likely reside. The user computing device 102 may additionally include a memory component 140, which stores modeling logic 144a and simulation logic 144b, described in more detail below.

The biomechanical measuring device 104 may include a probe 106 and may be configured as a device for measuring one or more aspects of the internal workings of the feminine body. As discussed in more detail below, the biomechanical measuring device 104 may be utilized to establish a baseline of data for establishing the inner workings of the feminine pelvic region. The data received from the biomechanical measuring device 104 may be compiled and sent to the user computing device 102 for creating simulations and designing products for women.

It should be understood that the biomechanical measuring device 104 and the probe 106 may take any form for capturing data on the internal pelvic environment. As an example, embodiments disclosed in U.S. Pat. Nos. 7,937,249 and 8,392,159, which are incorporated by reference in their entireties, may be utilized for this purpose. Other mechanisms for modeling the internal pelvic region of a model may also be utilized, such as magnetic resonance imaging (MRI), ultrasound, etc.

It should also be understood that while the user computing device 102 and the biomechanical measuring device 104 are each depicted as an individual devices, these are merely examples. Either of these devices may include one or more personal computers, servers, laptops, tablets, mobile computing devices, data storage devices, mobile phones, imaging devices, etc. that are configured for providing the functionality described herein. It should additionally be understood that other computing devices may also be included in the embodiment of FIG. 1. As an example, a consumer or product wearer may access data on the user computing device 102 via a different computing device to input specifications described below to receive product recommendations for those specifications.

Figure 2:
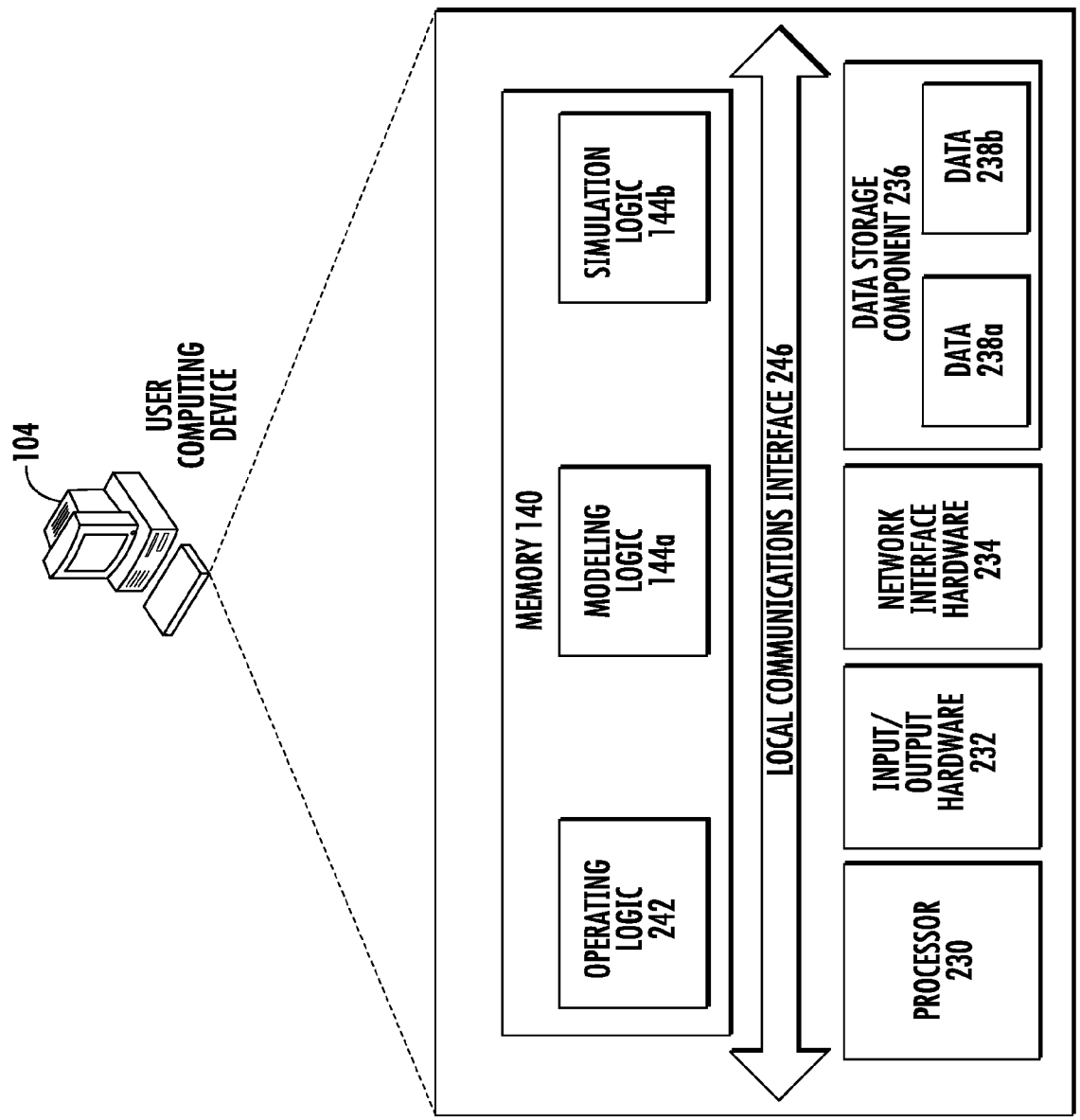
FIG. 2 depicts a user computing device for dynamically modeling the human internal pelvic region, according to embodiments disclosed herein.

FIG. 2 depicts the user computing device 102 for dynamically modeling the human internal pelvic region, according to embodiments disclosed herein. In the illustrated embodiment, the user computing device 102 includes a processor 230, input/output hardware 232, network interface hardware 234, a data storage component 236 (which stores video data 238a and state data 238b), and the memory component 140. The memory component 140 includes hardware and may be configured as volatile and/or nonvolatile memory and, as such, may include random access memory (including SRAM, DRAM, and/or other types of RAM), flash memory, registers, compact discs (CD), digital versatile discs (DVD), and/or other types of non-transitory computer-readable mediums. Depending on the particular embodiment, the non-transitory computer-readable medium may reside within the user computing device 102 and/or external to the user computing device 102.

Additionally, the memory component 140 may be configured to store operating logic 242, the modeling logic 144a, and the simulation logic 144b, each of which may be embodied as a computer program, firmware, and/or hardware, as an example. A local communications interface 246 is also included in FIG. 2 and may be implemented as a bus or other interface to facilitate communication among the components of the user computing device 102.

The processor 230 may include any hardware processing component operable to receive and execute instructions (such as from the data storage component 236 and/or memory component 140). The input/output hardware 232 may include and/or be configured to interface with a monitor, keyboard, mouse, printer, camera, microphone, speaker, and/or other device for receiving, sending, and/or presenting data. The network interface hardware 234 may include and/or be configured for communicating with any wired or wireless networking hardware, a satellite, an antenna, a modem, LAN port, wireless fidelity (Wi-Fi) card, WiMax card, mobile communications hardware, and/or other hardware for communicating with other networks and/or devices. From this connection, communication may be facilitated between the user computing device 102 and other computing devices.

Similarly, it should be understood that the data storage component 236 may reside local to and/or remote from the user computing device 102 and may be configured to store one or more pieces of data for access by the user computing device 102 and/or other components. In some embodiments, the data storage component 236 may be located remotely from the user computing device 102 and thus accessible via the network 100. In some embodiments however, the data storage component 236 may merely be a peripheral device, but external to the user computing device 102.

Included in the memory component 140 are the operating logic 242, the modeling logic 144a, and the simulation logic 144b. The operating logic 242 may include an operating system and/or other software for managing components of the user computing device 102. Similarly, the modeling logic 144a may be configured to cause the user computing device 102 to create one or more models of the pelvic region, based on the data received from the biomechanical measuring device 104. The simulation logic 144b may cause the user computing device 102 to run simulations based on dynamic actions that occur within the internal pelvic environment to design and redesign feminine products that provide the desired results.

It should be understood that the components illustrated in FIG. 2 are merely exemplary and are not intended to limit the scope of this disclosure. While the components in FIG. 2 are illustrated as residing within the user computing device 102, this is merely an example. In some embodiments, one or more of the components may reside external to the user computing device 102.

Figure 3:
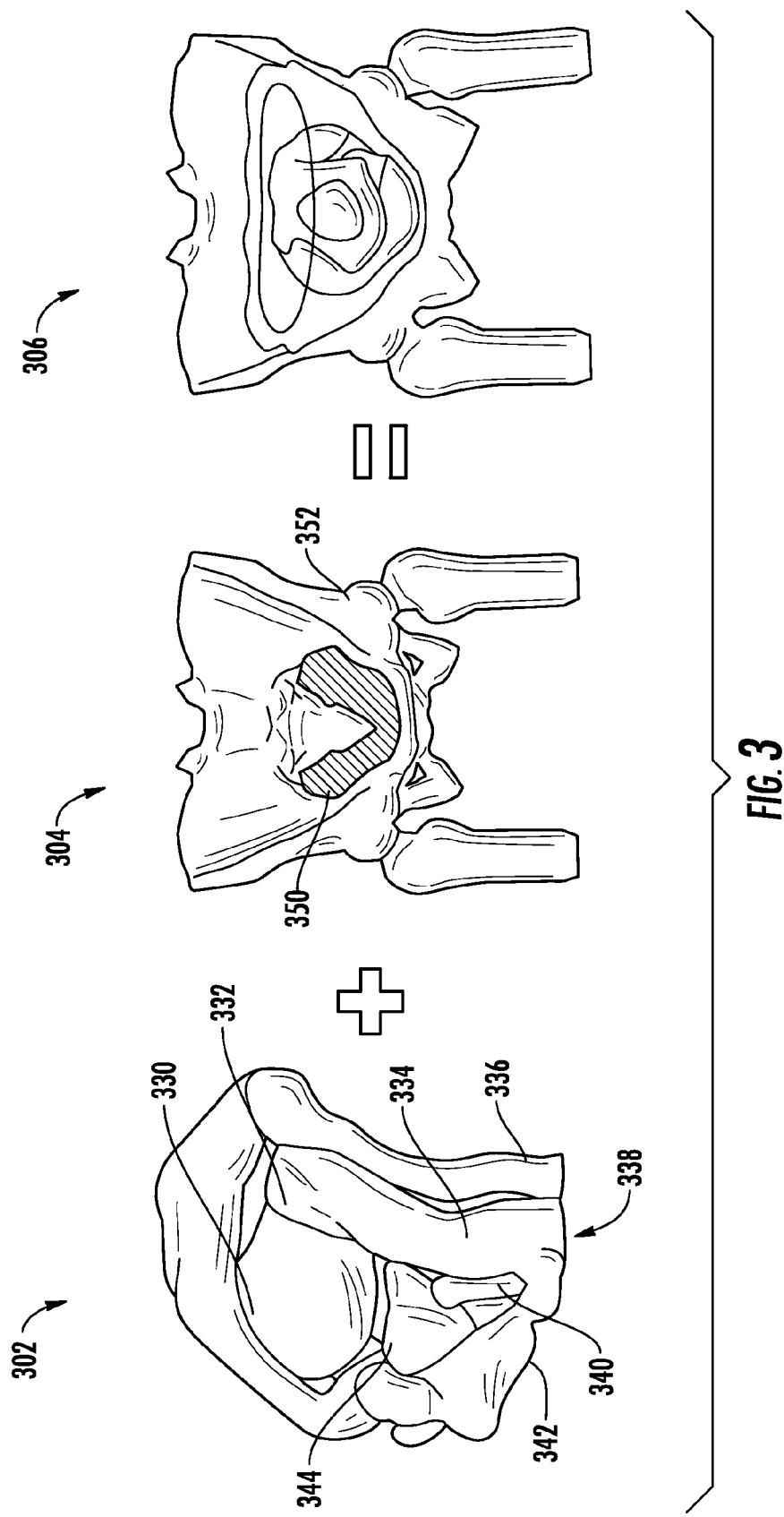
FIG. 3 depicts imagery of a representative dynamic model of the human internal pelvic region, according to embodiments disclosed herein.

FIG. 3 depicts imagery of a representative dynamic model of the human internal pelvic region, according to embodiments disclosed herein. As illustrated, a first model 302, which simulates a uterus 330, a cervix 332, a vagina 334, a rectum 336, an introits (vaginal opening) 338, a urethra 340, a pelvic bone 342, and a bladder 344. The first model 302 may be simulated by the user computing device 102, which may determine the size, shape, position, and/or other data for including in the simulation. The second model 304 may be utilized to simulate dynamic occurrences in the human pelvic region, such as the contraction of the pelvic floor muscles, which may also affect the organs in the model 302. Accordingly, the second model 304 may include the pelvic floor muscles 350 and the pelvis 352. Thus, the embodiments disclosed herein may utilize the organs of the first model 302 and the structure and muscles of the second model to generate a third model 306, which includes the portions of both the first model 302 and the second model 304 to determine the effectiveness of simulated feminine products in the pelvic environment.

Specifically, the user computing device 102 may determine the sizes and shapes of the various organs, structures, and muscles in the first model 302 and the second model 304, based on a desired body type and/or desired body size. Additionally, the user computing device 102 may be configured to simulate the interaction of simulated feminine product with the third model 306 to determine the comfort and effectiveness of the feminine product design. The interaction may include the pressures that the simulated pelvic region exerts on the third model 306 and vice versa. As also discussed herein, the interaction may include a simulation of one or more activities that the wearer of the feminine product may engage. As an example, the third model may represent a 30 year old female who participates in marathons and has not delivered a child. As such, the user computing device 102 may be configured to simulate insertion of a particular feminine product, as well has the movement and function of the feminine during activities that the model may participate.

Figure 4:
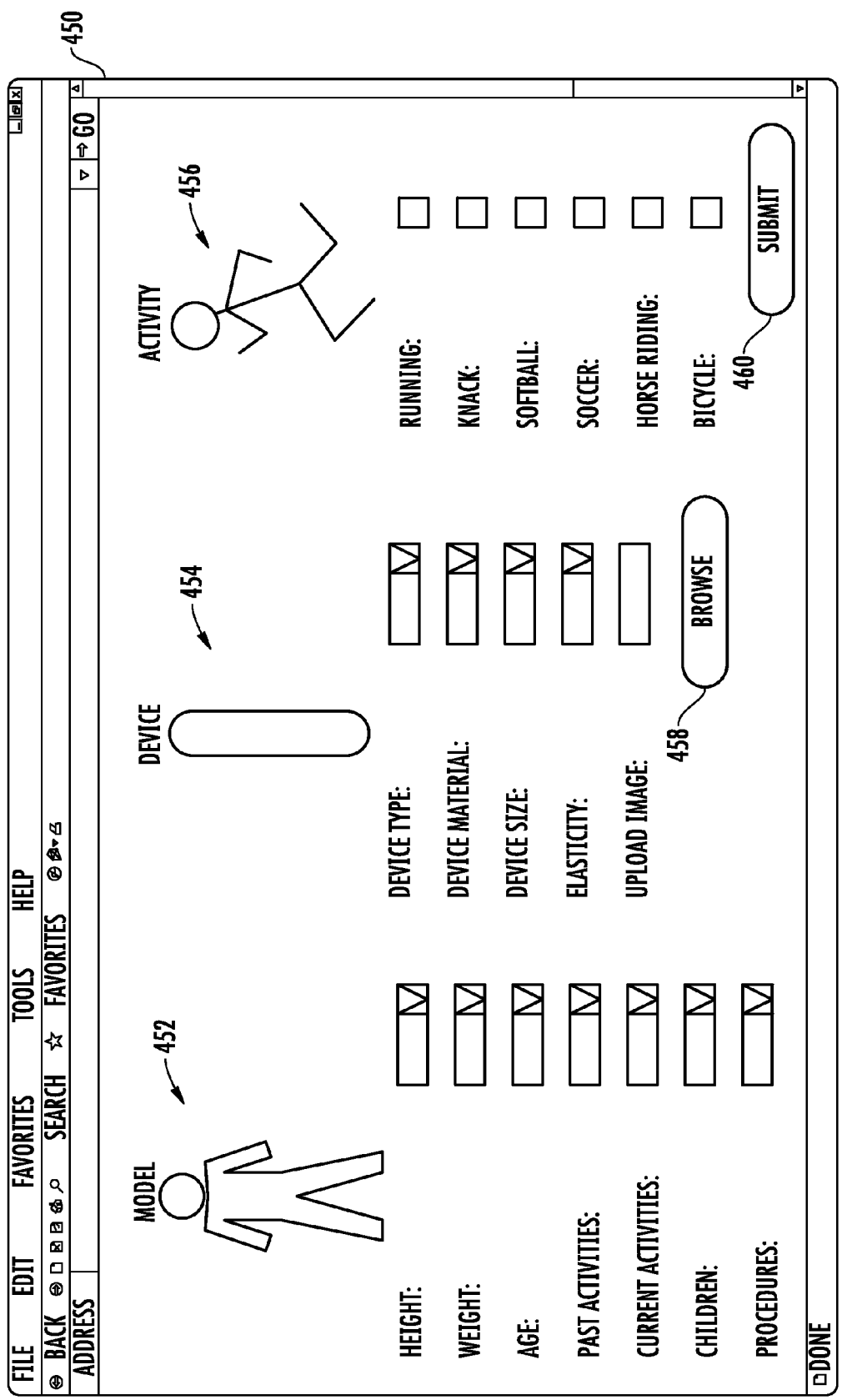
FIG. 4 depicts a user interface for selecting a model type, a device type and an activity type for dynamically modeling product interactions with the human internal pelvic region, according to embodiments disclosed herein.

FIG. 4 depicts a user interface 450 for selecting a model type, a device type, and an activity type for dynamically modeling product interactions with the human internal pelvic region, according to embodiments disclosed herein. As illustrated, the user interface 450 may be configured for a feminine product designer to set up a simulation to test a product design. Specifically, a user of the user computing device 102 may select one or more characteristics of a model in the model section 452. The model section 452 may represent a particular size, shape of woman, and/or other characteristics for designing a feminine product. As illustrated, the user may select height, weight, age, past activities, current activities, a number of children birthed, a number of children carried, medical procedures (such as an appendectomy, oophorectomy, cystoplasty, tubectomy, etc.), medical conditions that have impact on the pelvic floor muscles like chronic cough, lifestyle changes (diet, habits), and/or other features of the model that may be utilized to test a virtual design of a feminine product.

While the height, weight, and age fields are self explanatory, the past activities field may be utilized to identify activities or types of activities that the model participated in the past. As an example, the user may identify that the model was a high school athlete, a college athlete, and/or may specify one or more sports that the model participated at those levels. The current activities field may include similar types of information as the past activities field, with the difference being that the past activities field is utilized to identify a current condition of the model. The current activities field may also be utilized for determining the types of activities that the user will be participating while wearing the feminine product. The children field may be utilized for the user to identify whether the model has given birth and/or how many times the model has given birth. Other options, such as an option for specifying details of pregnancy (Caesarian section, twins, etc.). The procedures field may be utilized for the user to identify a medical procedure, medications, and/or other data for the model that may affect the health condition of the model.

As an example, if the user desires to design a feminine product for a woman who has had two children, played softball in college and now competes in triathlons, the user may select these characteristics for that particular model. This data may then be utilized to simulate a pelvic region that would include the selected parameters. The height, weight, body mass index (BMI), and/or other physiological conditions may be utilized to provide approximate size of the model's pelvic region, while age, past activities, children, and procedures may be utilized to customize the current condition of the model. The current activities may be used for this purpose and/or for determining the forces that the model will likely realize while wearing the feminine product.

Also included in the user interface 450 is a device section 454 that includes a device type field, a device material field, a device size field, and elasticity field, and an upload image field. Specifically, the device type field may be utilized for the user to identify the type of feminine device that may be simulated. As an example, the user may identify that a tampon, pessary, ring, feminine condom, pelvic muscle trainer, pelvic muscle stimulator, vaginal pressure sensor, pelvic muscle electromyogram sensor, vaginal dilator, ultrasound probe, balloon catheter, urethral slings, vaginal meshes, and/or other types of feminine and surgical product will be simulated. Additionally, the user may select the material that will be used for the feminine product. As an example, the user may identify that plastic, cotton, cardboard, rubber, and/or other material is used for the feminine device. Some embodiments are configured with a hierarchal structure, such that upon selection of the device type field, one or more options may be provided for selecting materials for each part of the feminine device, thus allowing for a plurality of types of materials for the feminine device.

Also included in the device section 454 are a device size field, a device elasticity field, and an upload image field. The device size field may be configured to receive one or more dimensions for the device (such as based on the particular components of the device). The elasticity may be similarly organized and may allow the user to provide information related to pliability, absorbency or other physical characteristic of the device. Some embodiments may also be configured to determine whether the feminine product that meets a desired physiological condition, such as pH, lubrication, menstrual flow protection, and resistance to biological environment.

The upload image field may allow the user to upload imagery and/or other data related to the device for populating the fields in the device section 454. As an example, the user may upload a data sheet that includes all features of the device. A browse option 458 may be utilized for the user to browse a local or network drive for a file that includes the desired device data.

Also included is an activity section 456. The activity section 456 provides options for selecting one or more activities, a frequency, and/or a duration of the activities of the model. As an example, the activity section 456 may relate to the past activities field and/or the current activities field. Thus, some embodiments may be configured disable the activity section 456 in response to no past activities or current activities being selected.

It should be understood that the activity section 456 may be utilized to customize the types of stresses and/or pressures that the feminine device may be subject. As an example, if the model plays soccer, the pelvic floor muscles, posture of the model, and impact to the body of the model may differ that when the same model is riding a bicycle. As a consequence, the user may select one or more of these activities for inclusion in the simulation. Also included is a submit option 460 for submitting the selected criteria to the user computing device 102.

It should also be understood that while in some embodiments the user interface 450 may be provided to a device designer, in some embodiments the user interface 450 may be provided to a consumer. Specifically, the user-consumer may access the user interface 450 for determining which commercially available device is best for the body type and activity level of the wearer. In such embodiments, the user-consumer may populate the fields in the user interface 450 and the user computing device 102 may return a desired feminine product and/or instructions for using the product. In embodiments where the user is a product designer, the user interface of FIG. 5 may be provided in response to selection of the submit option 460.

Figure 5:
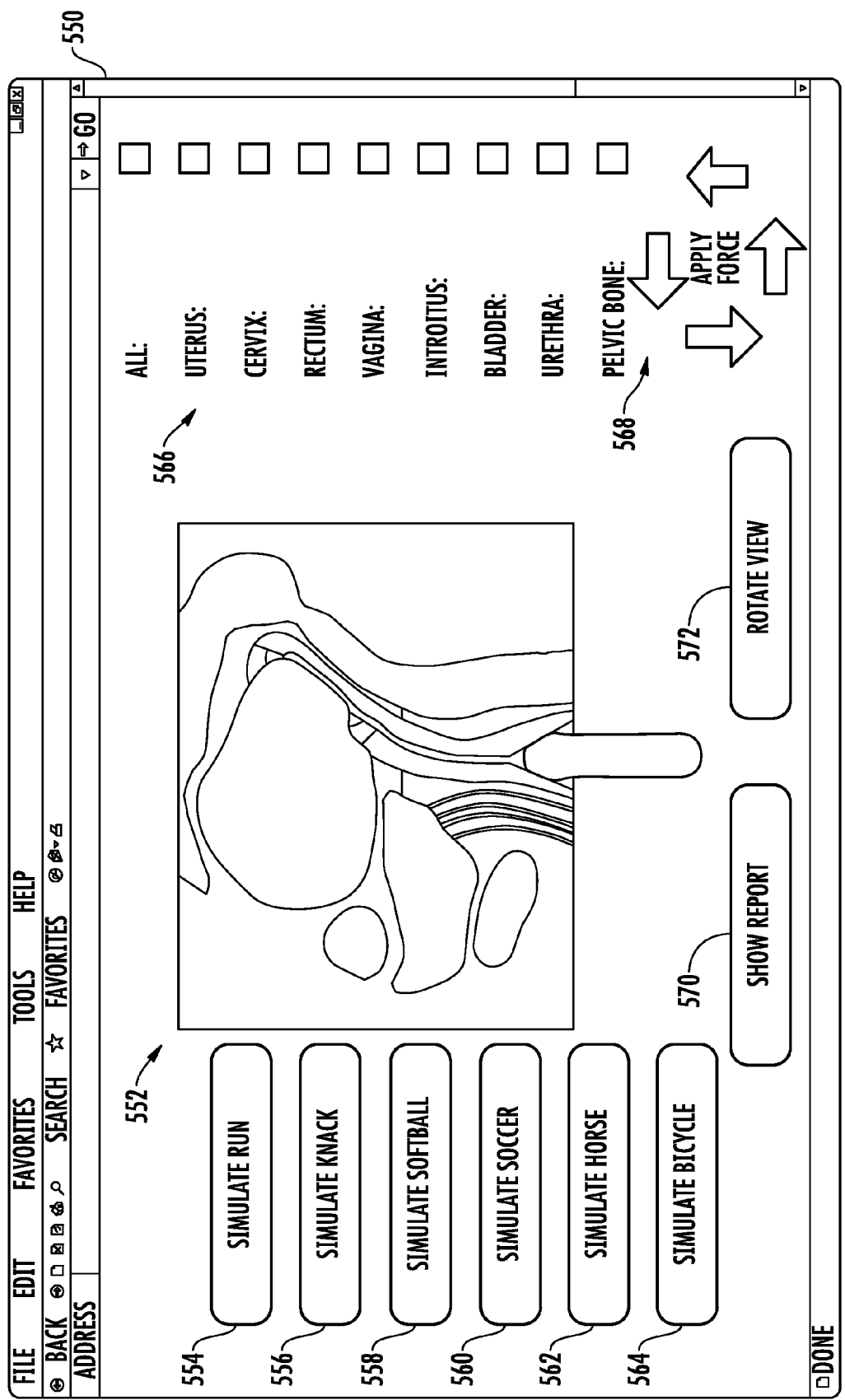
FIG. 5 depicts a user interface for simulating a plurality of different activities on the human internal pelvic region, according to embodiments disclosed herein.

FIG. 5 depicts a user interface 550 for simulating a plurality of different activities on the human internal pelvic region, according to embodiments disclosed herein. Based on the information provided in the user interface 450 in FIG. 4, the computational simulation 552, such as a 3-dimensional simulation may be provided, which provides biomechanical activity between a feminine product and the pelvic region. The computational simulation 552 may identify the pressure points of the feminine device when inserted into the pelvic region, as well as the position of the feminine device during and/or after one or more of the activities depicted in FIG. 4 and represented in the options of FIG. 5.

As an example, the computational simulation 552 may be configured to substantially represent the model height, weight, age, BMI and/or other characteristics selected in FIG. 4. Additionally, the selected feminine device may be virtually inserted and positioned as a wearer normally would. Additionally, the selected activity from FIG. 4 may be simulated such that a determination may be made regarding whether the design for the simulated feminine device provides the desired comfort and protection. Additionally, the user interface 550 includes a plurality of options to select one or more activities. Included are a simulate run option 554, a simulate KNACK exercises option 556, a simulate softball option 558, a simulate soccer option 560, a simulate horse riding option 562, and a simulate bicycling option 564. KNACK exercises are exercises that a female may perform to strengthen the pelvic floor muscles to reduce leakage and other ailments. As such, a wearer of feminine products may desire that certain products provide protection through various stages of competence in the KNACK exercises. By selecting the simulate KNACK exercises option 556, physical therapy exercises, such as KNACK exercises (or other exercises for strengthening the pelvic environment) may be simulated on the simulated model. Other options available include coughing, sneezing, laughing, jumping, falling, sitting, laying down, swimming, straining, running, automobile rides and bicycling. The car riding option simulates the pressure exerted by a seatbelt and may also include the impact of car crashes on the pelvic cavity. The birthing example simulates the pressures on the pelvic cavity due to deformations of the pelvic organs.

Also included are pelvic region force options 566 and 568. In addition to simulating a particular activity, the user interface 550 may be configured to cause the user computing device 102 to simulate particular forces on a specified area of the pelvic region. As an example, the user may manually select a uterus option, as well as a direction and may then apply a simulated force. This may provide the product designer with the ability to provide any force upon the feminine product to determine the comfort and/or reliability.

Also included are a show report option 570 and a rotate view option 572. In response to selection of the show report option 570, information regarding the position, deformation, comfort, and reliability of the simulated feminine product may be provided. In response to selection of the rotate view option 572, the computational simulation 552 (which may be a 3-dimensional simulation) may be rotated to provide a different viewing angle.

Figure 6:
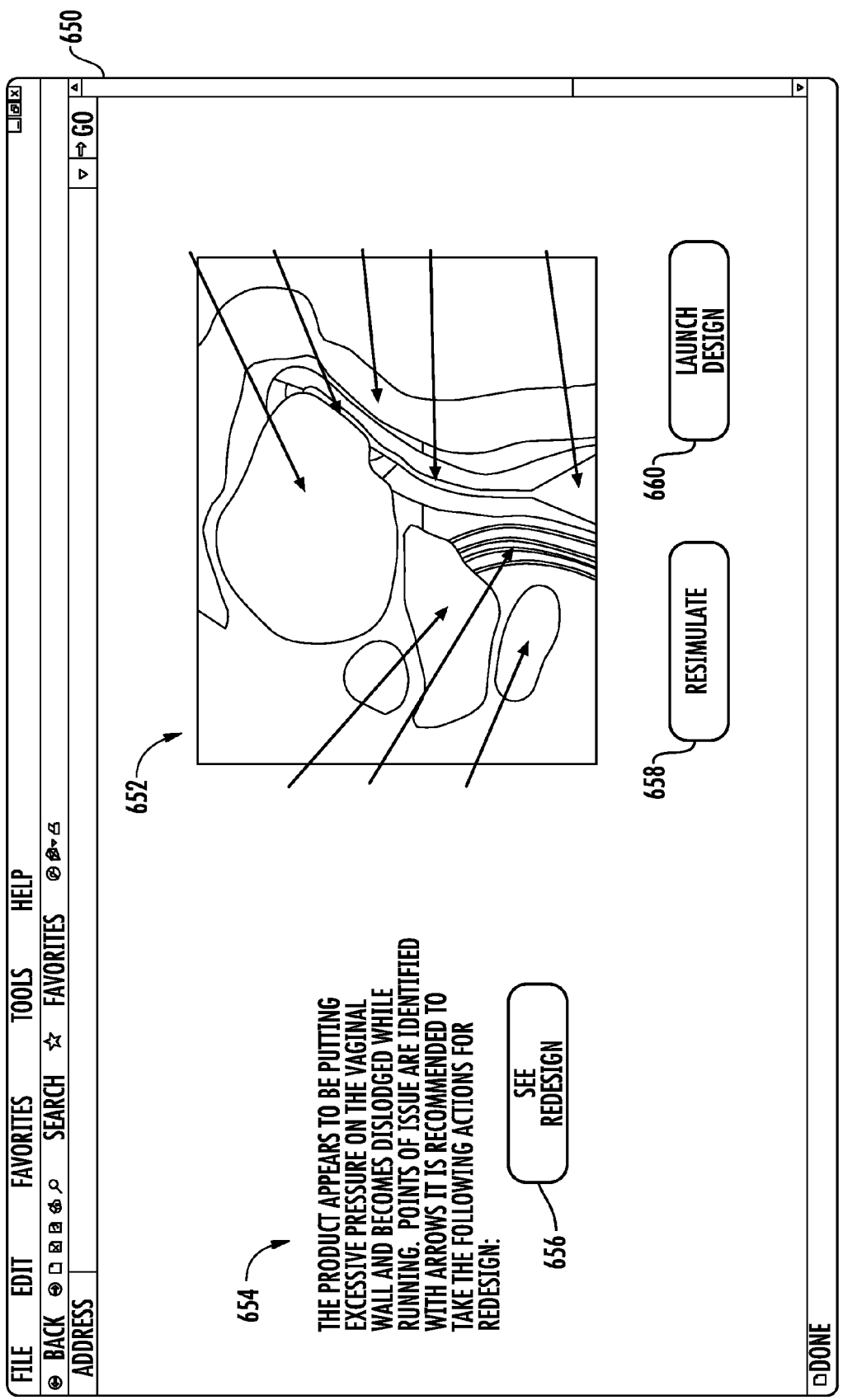
FIG. 6 depicts a user interface for providing issues regarding a selected product design, according to embodiments disclosed herein.

FIG. 6 depicts a user interface 650 for providing issues regarding a selected product design, according to embodiments disclosed herein. In response to selection of the show report option 570 from FIG. 5, the user interface 650 may be provided that includes a report of the effect that the feminine device has on the pelvic region of the virtual model. Specifically, a simulation window 652 may be provided that includes a similar representation of the model from FIG. 5, except that one or more indicators may be provided to highlight one or more areas that the feminine product causes an issue. Depending on the particular embodiment, the issue may include excessive pressure on an area of the pelvic region, not enough pressure on an area of the pelvic region, potential dislodging or misalignment, lack of absorbency, and/or other issues. Accordingly, a textual description 654 may be provided.

Also included are a see redesign option 656, a re-simulate option 658, and a launch design option 660. The see redesign option 656 may cause the user computing device 102 to determine and provide recommended redesigns that the user computing device 102 has recommended for overcoming the identified issues. In some embodiments, the user computing device 102 may automatically redesign the simulated feminine product, in response to selection of the see redesign option 656. In some embodiments, a user interface may be provided to describe and/or illustrate the recommended changes. In response to selection of the re-simulate option 658, the simulation may be run again with the current settings. In response to selection of the launch design option 660, a user interface may be provided for the product designer to change the design of the feminine product.

Figure 7:
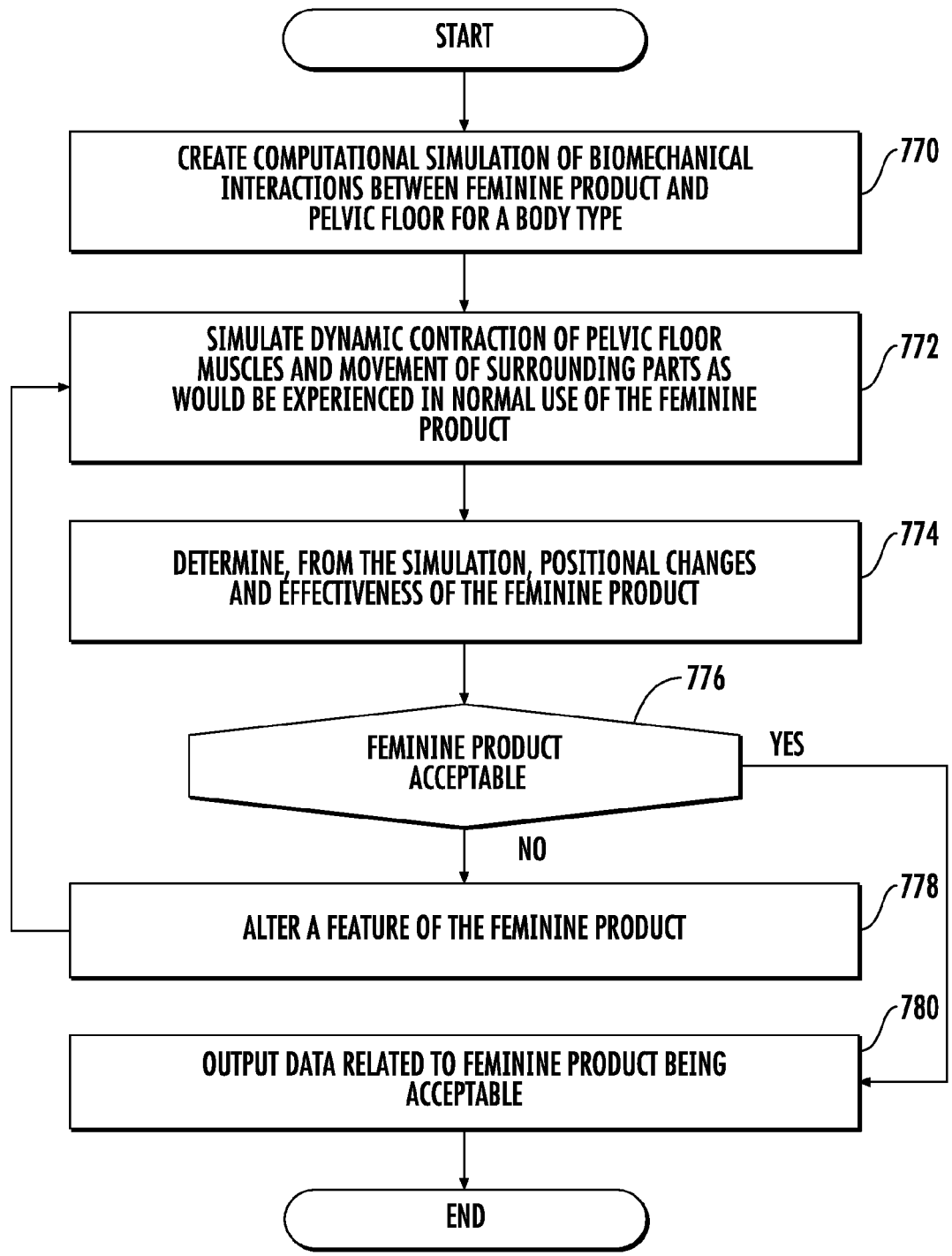
FIG. 7 depicts a flowchart depicting a process for determining whether a product design complies with a dynamic model of a human internal pelvic region, according to embodiments disclosed herein.

FIG. 7 depicts a flowchart depicting a process for determining whether a product design complies with a dynamic model of a human internal pelvic region, according to embodiments disclosed herein. As illustrated in block 770, a computation model of biomechanical interactions between a feminine product and the pelvic region for a model body type may be created. As described above, a simulation may be created that simulates a pelvic region of a model. The model may have a predetermined body type and/or characteristics. The feminine product may also be simulated to determine the interactions between the feminine product and the pelvic region during one or more activities. In block 772, dynamic contraction of pelvic floor muscles and movement of surrounding parts may be simulated, as may be experienced in normal use of the feminine product during the activities. In block 774, a determination may be made from the simulation regarding positional changes and effectiveness of the feminine product.

In block 776, a determination is made regarding whether the feminine product is acceptable. Depending on the particular embodiment, this decision may be made by a product designer and/or the user computing device 102, based on determined points of issue with the simulated feminine product. If not, the flowchart proceeds to block 778, were a feature of the feminine product is altered. From block 778, the flowchart returns to block 772. In response to the feminine product being acceptable in block 776, the flowchart may proceed to block 780, where data may be output related to the feminine product being acceptable.

Figure 8:
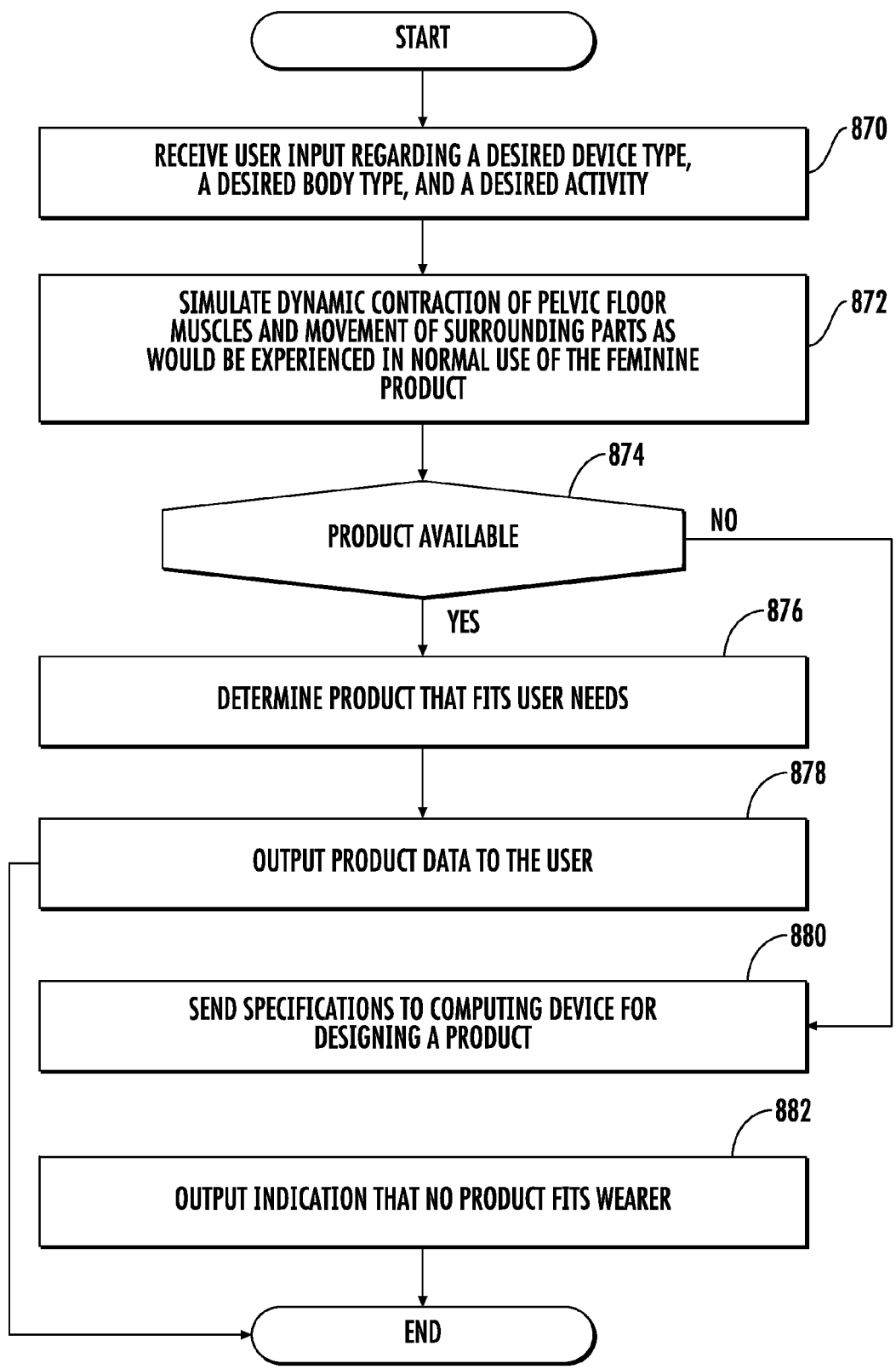
FIG. 8 depicts a flowchart depicting a process for determining a product design for a particular wearer, according to embodiments disclosed herein.

FIG. 8 depicts a flowchart depicting a process for determining a product design for a particular wearer, according to embodiments disclosed herein. As illustrated in block 870, a user input may be received regarding a desired product type, a desired body type, and a desired activity. In block 872, dynamic contraction of pelvic floor muscles and movement of surrounding parts may be simulated as would be experienced in normal use of the feminine product. In block 874, a determination is made regarding whether a product that will fit the wearer is available. If not, the flowchart proceeds to block 880, where specifications may be sent to a different computing device (such as the user computing device 102) for designing a new product. In block 882, an indication may be provided to the user that no product fits the wearer. If in block 874, the product is available, the flowchart proceeds to block 876, where a determination may be made regarding which product fits the wearer's needs. In block 878, product data may be output to the user.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mni" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be understood to those skilled in the art that various other changes and modifications can be made without departing from the spirit and scope of the invention. It is therefore intended to cover in the appended claims all such changes and modifications that are within the scope of this invention.

What is claimed is:

1. A method for dynamically modeling a human internal pelvic environment for product interactions, comprising:
   receiving, by a computing device, user input regarding a desired product type of a feminine product, a desired body type, and a desired activity;
   simulating, by the computing device, dynamic contraction of pelvic floor muscles and movement of surrounding parts as would be experienced in normal use of the feminine product;
   determining, by the computing device, whether the feminine product that meets the desired product type, the desired body type, and the desired activity is available for purchase;
   in response to determining that the feminine product that meets the desired product type, the desired body type, and the desired activity is available for purchase, outputting, by the computing device, an identification of the feminine product to a user; and
   in response to determining that the feminine product is not available for purchase, sending, by the computing device, data related to the user input to a different computing device for designing the feminine product and sending an output to the user indicating that no product is currently available.

2. The method of claim 1, wherein the desired product type comprises at least one of the following: a tampon, pessary, ring, feminine condom, pelvic muscle trainer, pelvic muscle stimulator, vaginal pressure sensor, pelvic muscle electromyogram sensor, vaginal dilator, ultrasound probe, and balloon catheter.

3. The method of claim 1, wherein the desired activity comprises a force that causes deformations of a pelvic cavity, including at least one of the following: coughing, sneezing, laughing, jumping, falling, sitting, laying down, swimming, straining, running, physical therapy exercises, pelvic floor exercises, softball, soccer, horse riding, birthing, amusement park rides, automobile rides and bicycling.

4. The method of claim 1, wherein the desired body type comprises at least one of the following: a height, a weight, an age, a past activity, a number of children birthed, a number of children carried, a medical condition, and a medical procedure.

5. The method of claim 1, wherein determining whether the feminine product meets the desired body type further comprises determining whether the feminine product will likely reposition during the desired activity.

6. The method of claim 1, wherein determining whether the feminine product meets the desired body type further comprises determining whether the feminine product exerts excessive pressure on a portion of a simulated pelvic region during the desired activity.

7. The method of claim 1, further comprising receiving an indication that the feminine product that meets the desired product type, body type, and activity.

8. The method of claim 1, further comprising determining whether the feminine product meets a desired physiological condition, including at least one of the following: pH, lubrication, menstrual flow protection, and resistance to biological environment.

* * * * *